(12) United States Patent
Pinkovich et al.

(10) Patent No.: US 11,200,456 B2
(45) Date of Patent: Dec. 14, 2021

(54) SYSTEMS AND METHODS FOR GENERATING AUGMENTED TRAINING DATA FOR MACHINE LEARNING MODELS

(71) Applicant: GE Precision Healthcare LLC, Milwaukee, WI (US)

(72) Inventors: Dani Pinkovich, Brookline, MA (US); Noa Alkobi, Haifa (IL); Sarit Shwartz, Haifa (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 215 days.

(21) Appl. No.: 16/528,490

(22) Filed: Jul. 31, 2019

(65) Prior Publication Data

US 2021/0034921 A1 Feb. 4, 2021

(51) Int. Cl.
| | |
|---|---|
| *G06K 9/62* | (2006.01) |
| *G06N 3/08* | (2006.01) |
| *G16H 50/20* | (2018.01) |
| *G06N 20/20* | (2019.01) |

(Continued)

(52) U.S. Cl.
CPC .............. *G06K 9/6257* (2013.01); *G06F 7/58* (2013.01); *G06K 9/6263* (2013.01); *G06N 3/08* (2013.01); *G06N 20/20* (2019.01); *G06T 5/003* (2013.01); *G16H 50/20* (2018.01)

(58) Field of Classification Search
CPC ...... G06K 9/6257; G06K 9/6263; G06N 3/08; G06N 20/20; G06N 3/0454; G16H 50/20; G16H 30/40; G06T 5/003; G06T 7/0012; G06F 7/58; A61B 8/14; A61B 8/5269;

(Continued)

(56) References Cited

U.S. PATENT DOCUMENTS

| | | | |
|---|---|---|---|
| 9,864,931 B2 * | 1/2018 | Kumar | G06K 9/6245 |
| 10,973,486 B2 * | 4/2021 | Sjostrand | A61B 6/5223 |
| 2016/0210749 A1 * | 7/2016 | Nguyen | G06N 3/0454 |

(Continued)

FOREIGN PATENT DOCUMENTS

| | | | | |
|---|---|---|---|---|
| WO | 2018011631 A2 | 1/2018 | | |
| WO | WO-2018011631 A2 * | 1/2018 | ........... | A61B 8/4416 |

(Continued)

*Primary Examiner* — Mahendra R Patel
(74) *Attorney, Agent, or Firm* — McCoy Russell LLP

(57) ABSTRACT

Methods and systems are provided for augmenting ultrasound image training data, which may be used to train one or more machine learning models. One example method for augmenting ultrasound training data comprises, selecting an ultrasound image and a ground truth output corresponding to the ultrasound image, determining a first modification to apply to the ultrasound image, applying the first modification to the ultrasound image to produce an augmented ultrasound image, modifying the ground truth output based on the first modification to produce an augmented ground truth output corresponding to the augmented ultrasound image, and training a machine learning model using the augmented ultrasound image and the augmented ground truth output. In this way, a machine learning model may learn a more robust mapping from ultrasound image features to expected output, with less probability of overfitting, and with increased generalizability to noisy ultrasound images, or ultrasound images containing artifacts.

20 Claims, 7 Drawing Sheets

(51) Int. Cl.
  *G06T 5/00*      (2006.01)
  *G06F 7/58*      (2006.01)
(58) Field of Classification Search
  CPC .................... A61B 6/032; A61B 6/037; H06T 2207/20084
  USPC ......................................................... 382/156
  See application file for complete search history.

(56)  References Cited

U.S. PATENT DOCUMENTS

| 2017/0337682 | A1* | 11/2017 | Liao     | G06T 7/30      |
| 2018/0028153 | A1* | 2/2018  | Kuroiwa  | A61B 8/488     |
| 2018/0247227 | A1* | 8/2018  | Holtham  | G06K 9/6215    |
| 2018/0315188 | A1* | 11/2018 | Tegzes   | G06K 9/2054    |
| 2019/0065884 | A1* | 2/2019  | Li       | G06K 9/6267    |
| 2019/0291277 | A1* | 9/2019  | Oleynik  | B25J 9/1669    |
| 2019/0311478 | A1* | 10/2019 | Avendi   | G06K 9/726     |
| 2019/0339688 | A1* | 11/2019 | Cella    | G05B 19/41865  |
| 2020/0151513 | A1* | 5/2020  | Lee      | G06K 9/6256    |
| 2020/0342600 | A1* | 10/2020 | Sjostrand| G06N 3/08      |
| 2020/0405269 | A1* | 12/2020 | Swisher  | G06N 3/04      |

FOREIGN PATENT DOCUMENTS

| WO | 2018048507 A1   | 3/2018 | |
| WO | WO-2018048507 A1 * | 3/2018 | ......... G01R 33/5608 |

* cited by examiner

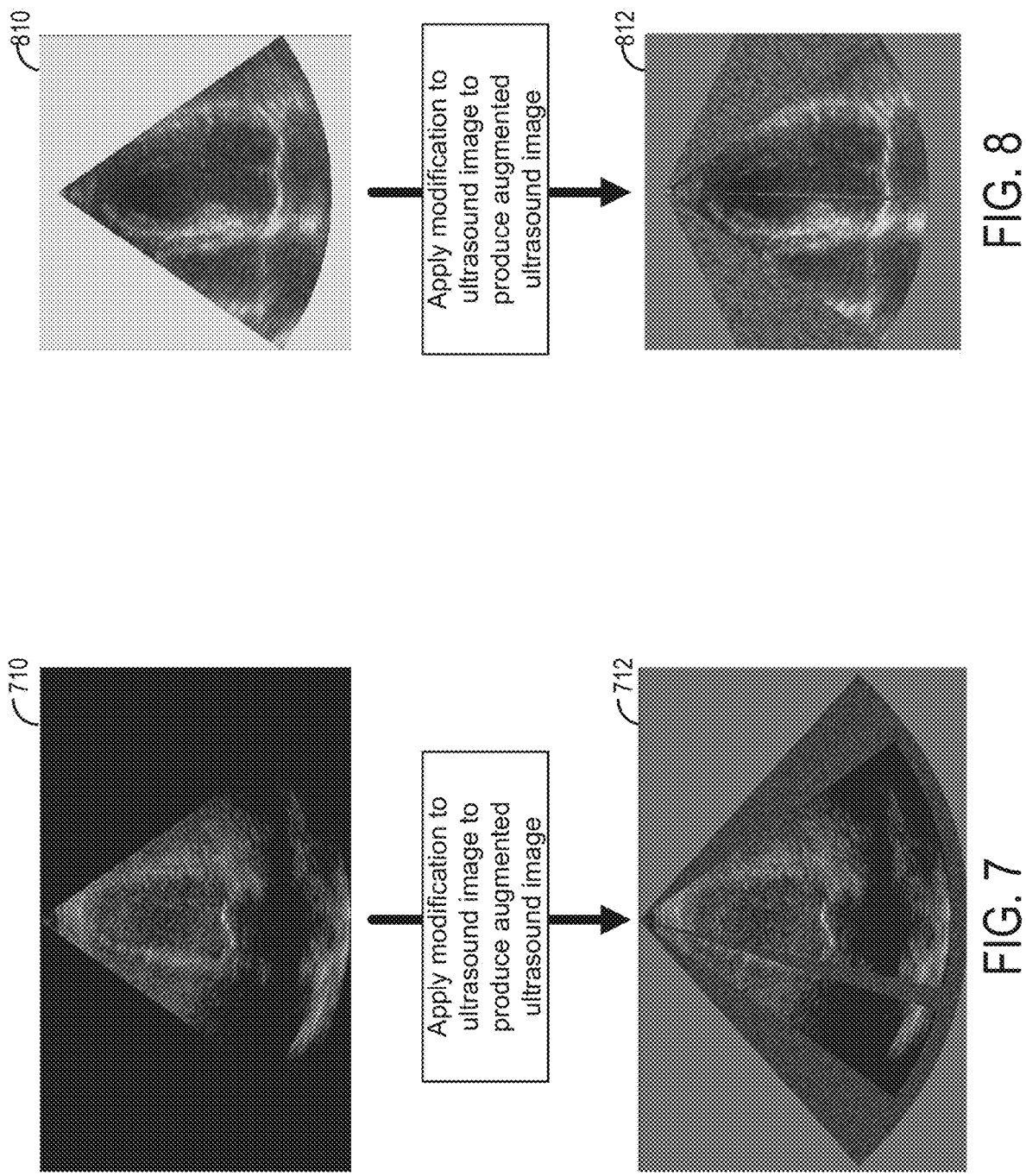

SYSTEMS AND METHODS FOR GENERATING AUGMENTED TRAINING DATA FOR MACHINE LEARNING MODELS

TECHNICAL FIELD

Embodiments of the subject matter disclosed herein relate to ultrasound imaging, and more particularly, to systems and methods for generating augmented training data for training machine learning models to process ultrasound images.

BACKGROUND

Machine learning models are routinely employed in the field of medical image processing and medical image analysis. In one example, machine learning models may be used to reduce blur in a medical image, produce super resolution medical images, diagnose a pathology based on a medical image, segment a medical image into different anatomical regions, or perform other types of image processing or analysis. Machine learning models may be trained using a training dataset, comprising pairs of input data and expected output data corresponding to the input data. Parameters of the model may be adjusted until a threshold degree of accuracy of the model output is achieved, where output accuracy is determined based on the difference between the model output and the expected output, or until the model parameters converge to a minimum error rate (or maximum accuracy) for the training dataset.

The ability of a trained machine learning model to map a given input to an appropriate output is known to be a function of the size of the training data set, and sparsity of training data is a generally recognized limitation in the field of machine learning. Further, using a finite set of training data may result in machine learning models which perform with significantly less fidelity on data which deviates, even in minor ways, from the data used during training. Thus, exploring techniques for increasing an amount of training data, and improving machine learning model robustness and generalizability, is generally desired.

SUMMARY

The present disclosure at least partially addresses the issues described above. In one embodiment, a method for augmenting ultrasound training data comprises, selecting an ultrasound image and a ground truth output corresponding to the ultrasound image, determining a first modification to apply to the ultrasound image, applying the first modification to the ultrasound image to produce an augmented ultrasound image, modifying the ground truth output based on the first modification to produce an augmented ground truth output corresponding to the augmented ultrasound image, and training a machine learning model using the augmented ultrasound image and the augmented ground truth output. In this way, a machine learning model may learn a more robust mapping from ultrasound image features to expected output, with less probability of overfitting, and with increased generalizability to noisy ultrasound images, or ultrasound images containing artifacts.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which:

FIG. 7 shows a first ultrasound image and a corresponding augmented ultrasound image produced by applying modifications to the first ultrasound image; and FIG. 8 shows a second ultrasound image and a corresponding augmented ultrasound image produced by applying modifications to the second ultrasound image.

Figure 1:
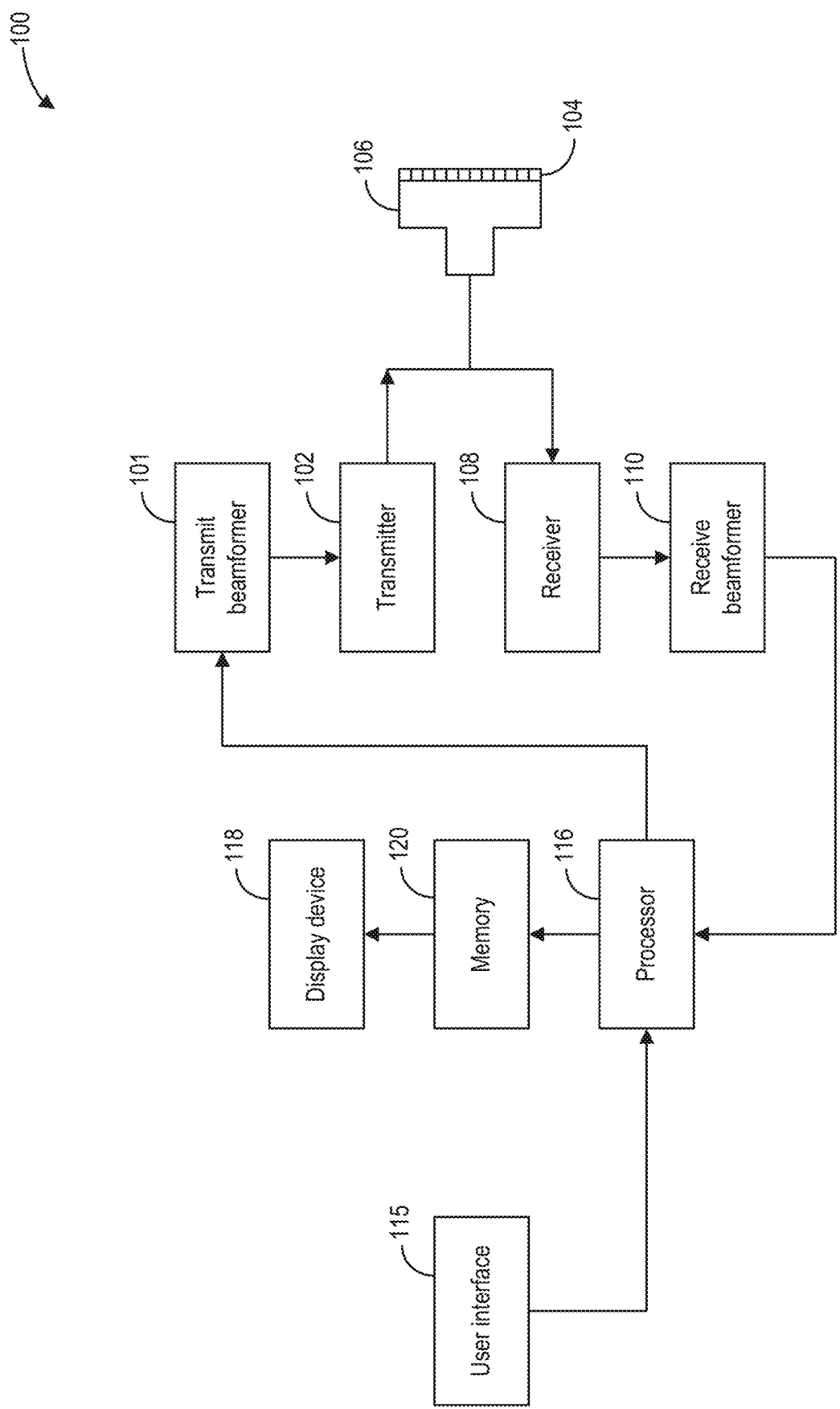
FIG. 1 shows a block diagram of an exemplary embodiment of an ultrasound system.

The drawings illustrate specific aspects of the described systems and methods for augmenting ultrasound data to increase machine learning model robustness and generalizability. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems and methods.

DETAILED DESCRIPTION

The following description relates to various embodiments for increasing machine learning model generalizability and robustness by applying one or more ultrasound specific modifications to ultrasound images within an ultrasound image training data set. In some embodiments, an ultrasound image acquired by an ultrasound system (such as the ultrasound system of FIG. 1) may be augmented by an image processing system, such as the image processing system shown in FIG. 2. The augmented ultrasound training data produced by the image processing system may be used to train a deep learning network, or other machine learning model, such as the deep learning network illustrated schematically in FIG. 3, which in some embodiments may be stored in non-transitory memory of the image processing system of FIG. 2. The image processing system may generate augmented ultrasound images and augmented ground truth output by executing instructions stored in non-transitory memory, wherein the instructions may cause the image processing system to execute one or more of the steps of method 400 shown in FIG. 4, method 500 shown in FIG. 5, and/or method 600 shown in FIG. 6. FIGS. 7 and 8 show example ultrasound images, and augmented ultrasound images produced from the ultrasound images by applying one or more modifications, such as according to method 400 shown in FIG. 4.

In some embodiments, augmentations are applied randomly or pseudo-randomly to ultrasound images within a training data set, wherein the applied augmentations/modifications mimic/simulate one or more variations likely to occur within ultrasound imaging, such as a variation of image depth, azimuthal angle of the image, and/or by applying ultrasound specific image artifacts or orientation changes. In this way each training data pair within an ultrasound image training data set may be augmented to produce a significantly larger augmented training data set. In some embodiments, each training data pair may be augmented repeatedly, wherein each augmentation may be unique, thereby enabling a machine learning model to train continuously on novel data, produced from a finite pool of ultrasound data. In one embodiment, modifications are determined based on random or pseudo-randomly generated numbers, such that a probability of a same modification being selected and applied to a same ultrasound image is reduced. Further, in some embodiments, a plurality of modifications, each randomly selected, may be applied to each ultrasound image, wherein the probability of a same augmented ultrasound image being produced drops exponentially with the number of the plurality of modifications applied. In this way, a machine learning model may learn a more robust mapping from ultrasound image features to expected output, with less probability of overfitting, and with increased generalizability to noisy ultrasound images, or ultrasound images containing artifacts.

Referring to FIG. 1, a schematic diagram of an ultrasound imaging system 100 in accordance with an embodiment of the invention is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be deblurred, segmented, etc. by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat".

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set, for training one or more machine learning models, wherein the machine learning models may be used to perform one or more steps of ultrasound image processing.

Figure 2:
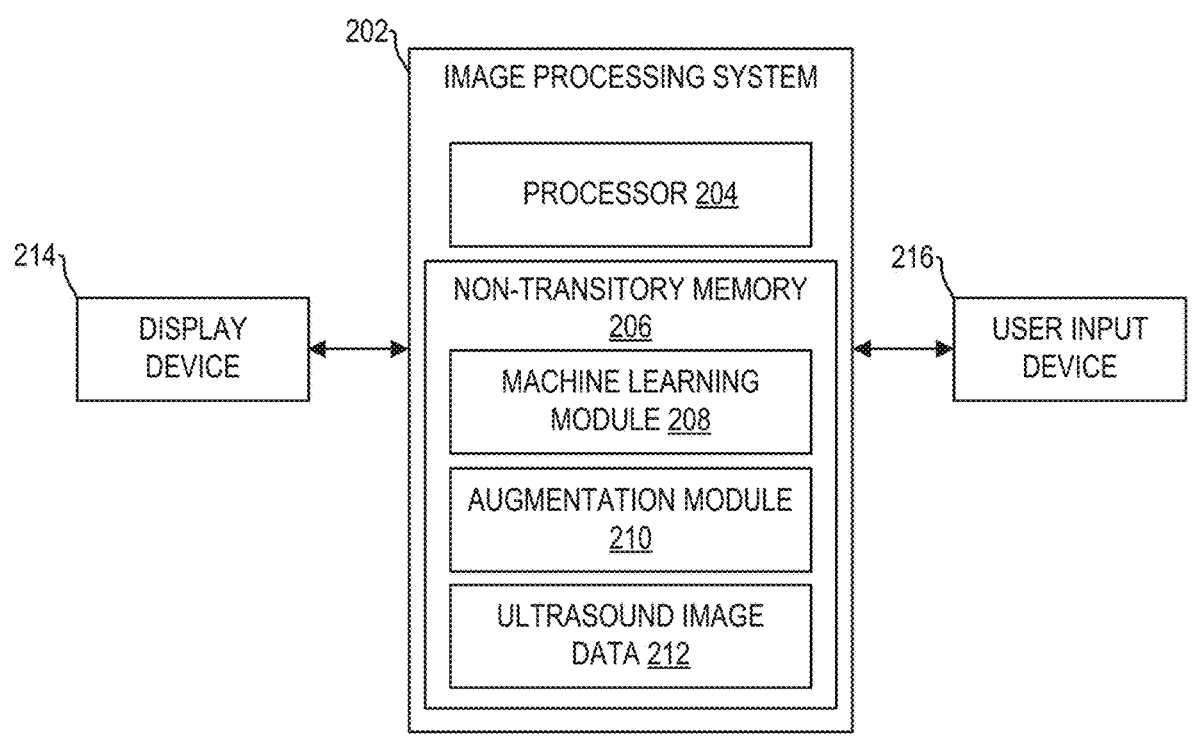
FIG. 2 is a schematic diagram illustrating a system for augmenting ultrasound training data, according to an exemplary embodiment.

Referring to FIG. 2, image processing system 202 is shown, in accordance with an exemplary embodiment. In some embodiments, image processing system 202 is incorporated into the ultrasound imaging system 100. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may comprise a user input device 214, and display device 216.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store machine learning module 208, augmentation module 210, and ultrasound image data 212. Machine learning module 208 may include one or more deep learning networks, comprising a plurality of weights and biases, activation functions, loss functions, gradient descent algorithms, and instructions for implementing the one or more deep neural networks to process an input ultrasound image. For example, machine learning module 208 may store instructions for training and implementing a neural network, such as the convolutional neural network (CNN) of CNN architecture 300, shown in FIG. 3. Machine learning module 208 may include trained and/or untrained neural networks and may further include training routines, or parameters (e.g., weights and biases), associated with one or more neural network models stored therein.

Figure 4:
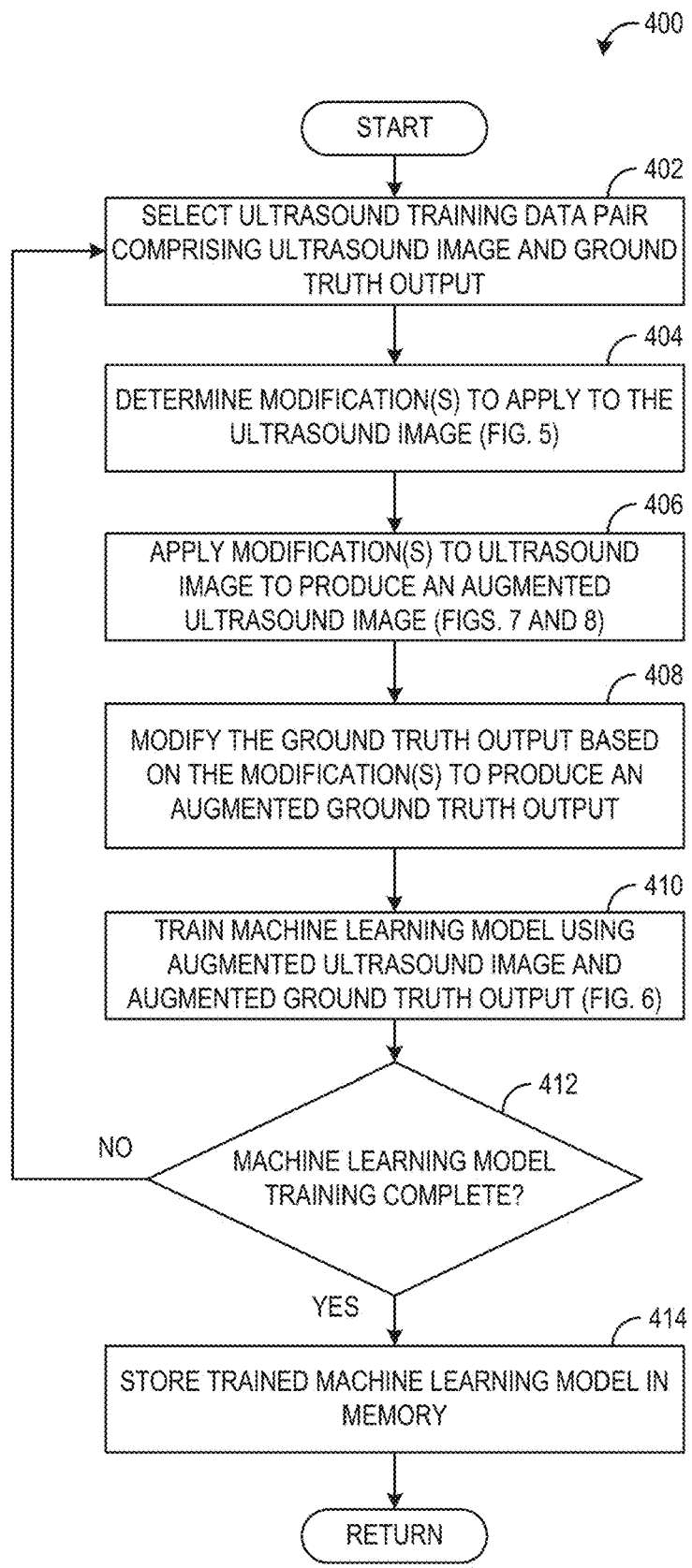
FIG. 4 is a flow chart illustrating a method for generating augmented ultrasound training data, according to an exemplary embodiment.

Non-transitory memory 206 may further include augmentation module 210, which may be configured to select un-augmented or augmented ultrasound training data, and modify it by selecting and applying one or more modifications, such as is described in more detail in FIG. 4. In one example, augmentation module 210 is configured to select training data pairs stored in ultrasound image data 212, modify the training data pairs according to one or more methods disclosed herein, and use the augmented training data pair to train a machine learning model stored in machine learning module 208.

Non-transitory memory 206 may further store ultrasound image data 212, such as ultrasound images captured by the ultrasound imaging system of FIG. 1. For example, ultrasound image data 212 may store augmented and un-augmented ultrasound images, augmented and un-augmented ground truth output, and other types of ultrasound image data. In some embodiments, ultrasound image data 212 may store ultrasound images and ground truth output in an ordered format, such that each ultrasound image is associated with one or more corresponding ground truth outputs.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

Image processing system 202 may further include user input device 216. User input device 216 may comprise one or more of a touchscreen, a keyboard, a mouse, a trackpad, a motion sensing camera, or other device configured to enable a user to interact with and manipulate data within image processing system 31. In one example, user input device 216 may enable a user to make a selection of an ultrasound image to use in training a machine learning model, or for further processing using a trained machine learning model.

Display device 214 may include one or more display devices utilizing virtually any type of technology. In some embodiments, display device 214 may comprise a computer monitor, and may display augmented and or un-augmented ultrasound images. Display device 214 may be combined with processor 204, non-transitory memory 206, and/or user input device 216 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3:
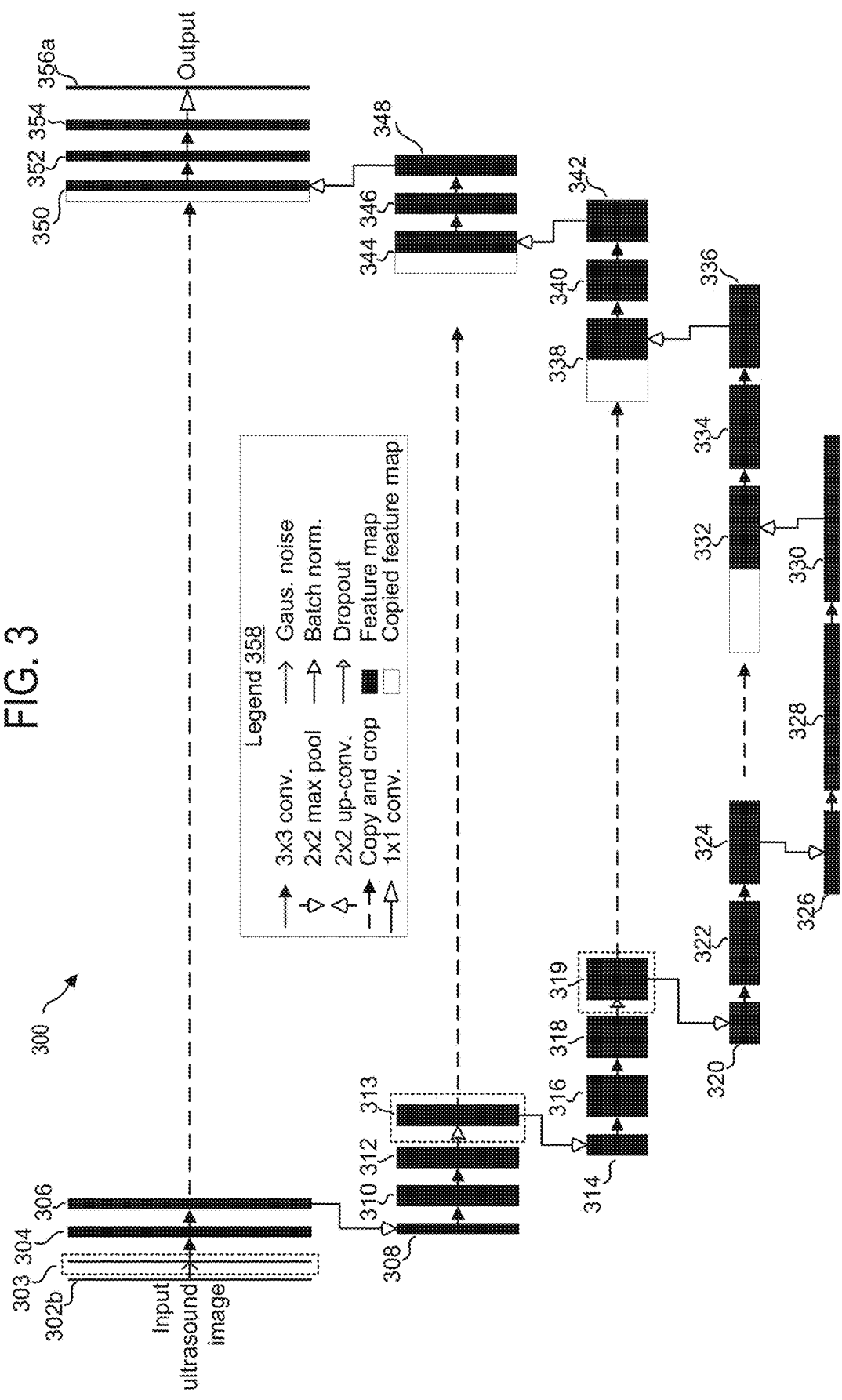
FIG. 3 is a schematic diagram illustrating the layout of a deep learning network which may be trained using the augmented ultrasound data produced by the system of FIG. 2, according to an exemplary embodiment.

Turning to FIG. 3, CNN architecture 300 is shown. CNN architecture 300 represents one example of a machine learning model according to the current disclosure, wherein the parameters of CNN 300 may be learned using augmented training data produced according to one or more methods disclosed herein. CNN 300 comprises a U-net architecture, which may be divided into an autoencoder portion (descending portion, elements 302b-330) and an autodecoder portion (ascending portion, elements 332-356a). CNN architecture 300 is configured to receive ultrasound images comprising a plurality of pixels/voxels, and map the input ultrasound image to a pre-determined type of output. In one embodiment, CNN 300 may be configured to segment an input ultrasound image into foreground and background. In another embodiment, CNN 300 may be map a blurred ultrasound image to a deblurred ultrasound image. CNN architecture 300 includes a series of mappings, from an input image tile 302b which may be received by an input layer, through a plurality of feature maps, and finally to an output layer 356a.

The various elements comprising CNN architecture 300 are labeled in legend 358. As indicated by legend 358, CNN architecture 300 includes a plurality of feature maps (and/or copied feature maps), wherein each feature map may receive input from either an external file, or a previous feature map, and may transform/map the received input to output to produce a next feature map. Each feature map may comprise a plurality of neurons, where in some embodiments, each neuron may receive input from a subset of neurons of a previous layer/feature map, and may compute a single output based on the received inputs, wherein the output may be propagated to a subset of the neurons in a next layer/feature map. A feature map may be described using spatial dimensions, such as length, width, and depth, wherein the dimensions refer to the number of neurons comprising the feature map (e.g., how many neurons long, how many neurons wide, and how many neurons deep, a specified feature map is).

In some embodiments, the neurons of the feature maps may compute an output by performing a dot product of received inputs using a set of learned weights (each set of learned weights may herein be referred to as a filter), wherein each received input has a unique corresponding learned weight, wherein the learned weight was learned during training of the CNN.

The transformations/mappings performed by each feature map are indicated by arrows, wherein each type of arrow corresponds to a distinct transformation, as indicated by legend 358. Rightward pointing solid black arrows indicate 3×3 convolutions with stride of one, wherein output from a 3×3 grid of feature channels of an immediately preceding feature map are mapped to a single feature channel of a current feature map. Each 3×3 convolution may be followed by an activation function, wherein, in one embodiment, the activation function comprises a rectified linear unit (ReLU).

Downward pointing hollow arrows indicate 2×2 max pooling, wherein the max value from a 2×2 grid of feature channels is propagated from an immediately preceding feature map to a single feature channel of a current feature map, thereby resulting in a 4-fold reduction in spatial resolution of the immediately preceding feature map.

Upward pointing hollow arrows indicate 2×2 up-convolutions, which comprise mapping output from a single feature channel of an immediately preceding feature map to a 2×2 grid of feature channels in a current feature map, thereby increasing the spatial resolution of the immediately preceding feature map 4-fold.

Rightward pointing dash-tailed arrows indicate copying and cropping of a feature map for concatenation with another, later occurring, feature map. Cropping enables the dimensions of the copied feature map to match the dimensions of the feature map with which the copied feature map is to be concatenated. It will be appreciated that when the size of the first feature map being copied and the size of the second feature map to be concatenated with the first feature map, are equal, no cropping may be performed.

Rightward pointing arrows with hollow elongated triangular heads indicate a 1×1 convolution, in which each feature channel in an immediately preceding feature map is mapped to a single feature channel of a current feature map, or in other words, wherein a 1-to-1 mapping of feature channels between an immediately preceding feature map and a current feature map occurs.

Rightward pointing arrows with chevron heads indicate incorporation of Gaussian noise into a received input feature map.

Rightward pointing arrows with arcuate hollow heads indicate batch normalization operations, wherein a distribution of activations of an input feature map are normalized.

Rightward pointing arrows with a short hollow triangular head indicates a dropout operation, wherein random or pseudo-random dropout of input neurons (as well as their inputs and outputs) occurs during training.

In addition to the operations indicated by the arrows within legend 358, CNN architecture 300 includes solid filled rectangles corresponding to feature maps, wherein feature maps comprise a height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a left-right length as shown in FIG. 3, corresponds to the number of features within each feature channel). Likewise, CNN architecture 300 includes hollow (unfilled) rectangles, corresponding to copied and cropped feature maps, wherein copied feature maps comprise height (top to bottom length as shown in FIG. 3, corresponds to a y spatial dimension in an x-y plane), width (not shown in FIG. 3, assumed equal in magnitude to height, corresponds to an x spatial dimension in an x-y plane), and depth (a length from a left side to a right side as shown in FIG. 3, corresponds to the number of features within each feature channel).

Starting at input image tile 302b (herein also referred to as an input layer), data corresponding to an ultrasound image, may be input and mapped to a first set of features. In some embodiments, the input data is pre-processed (e.g., normalized) before being processed by the neural network. The weights/parameters of each layer of CNN 300 may be learned during a training process, wherein matched pairs of input and expected output (ground truth output) are fed to CNN 300. Parameters may be adjusted based on a gradient descent algorithm, or other algorithm, until the output of CNN 300 matches the expected output (the ground truth output) within a threshold degree of accuracy.

As indicated by the rightward pointing chevron headed arrow immediately to the right of input image tile 302b, a Gaussian noise incorporation operation is optionally conducted on the output of the input image tile 302b. The Gaussian noise incorporation operation introduces additive, zero centered Gaussian noise during training to data output from input image tile 302b to feature map 303. Feature map 303 may comprise the same dimensions as the input with the same depth as input image tile 302b. By incorporating Gaussian noise in a random, or pseudo random manner into input image data, a probability of overfitting may be reduced during training of CNN 300.

As indicated by the solid black rightward pointing arrow immediately to the right of feature map 303, a 3×3 convolution of the feature channels of feature map 303 is performed to produce feature map 304. As discussed above, a 3×3 convolution includes mapping input from a 3×3 grid of feature channels to a single feature channel of a current feature map, using learned weights, wherein the learned weights are referred to as a convolution filter. Each 3×3 convolution in CNN architecture 300 may include a subsequent activation function, which in one embodiment includes passing the output of each 3×3 convolution through a ReLU. In some embodiments, activation functions other than ReLUs may be employed, such as Softplus (also referred to as SmoothReLUs), leaky ReLUs, noisy ReLUs, exponential linear units (ELUs), Tan h, Gaussian, Sinc, Bent identity, logistic functions, and other activation functions known in the art of machine learning.

As indicated by the solid black rightward pointing arrow immediately to the right of feature map 304, a 3×3 convolution is performed on feature map 304 to produce feature map 306.

As indicated by the downward pointing arrow beneath feature map 306, a 2×2 max pooling operation is performed on feature map 306 to produce feature map 308. Briefly, a 2×2 max pooling operation includes determining a max feature value from a 2×2 grid of feature channels of an immediately preceding feature map, and setting a single feature, in a single feature channel, of a current feature map, to the max value so determined. Additionally, feature map 306 is cropped, copied, and concatenated with output from feature map 348 to produce feature map 350, as indicated by the dash-tailed rightward pointing arrow immediately to the right of feature map 306.

As indicated by the solid black rightward pointing arrow immediately to the right of feature map 308, a 3×3 convolution with stride 1 is performed on feature map 308 to produce feature map 310.

As indicated by the solid black rightward pointing arrow immediately to the right of feature map 310, a 3×3 convolution with stride 1 is performed on feature map 310 to produce feature map 312.

As indicated by the rightward pointing hollow headed arcuate arrow immediately to the right of feature map 312, an optional batch normalization operation is conducted on the output of feature map 312 to produce feature map 313. In batch normalization, the outputs of feature map 312 are normalized across a mini-batch to speed up training of CNNs and reduce the sensitivity to network initialization. Batch normalization operations normalize the activations of each channel by subtracting the mini-batch mean and dividing by the mini-batch standard deviation. Then, the batch operation shifts the input by a learnable offset $\beta$ and scales it by a learnable scale factor $\gamma$.

As indicated by the downward pointing hollow headed arrow beneath feature map 313, a 2×2 max pooling operation is performed on feature map 313 to produce feature map 314, wherein feature map 314 is of one fourth the spatial resolution of feature map 312. Additionally, feature map 313 is copied, cropped, and concatenated with output from feature map 342 to produce feature map 344, as indicated by the dash-tailed rightward pointing arrow immediately to the right of feature map 313.

As indicated by the solid black rightward pointing arrow immediately to the right of feature map 314, a 3×3 convolution with stride 1 is performed on feature map 314 to produce feature map 316.

As indicated by the solid black rightward pointing arrow immediately to the right of feature map 316, a 3×3 convolution with stride 1 is performed on feature map 316 to produce feature map 318.

As indicated by the rightward pointing short hollow headed triangular arrow immediately to the right of feature map 318, an optional dropout operation is performed during training, wherein a random or pseudo random subset of input activations/features are removed/deleted for a given iteration of training, thereby reducing a probability of CNN 300 overfitting the training data.

As indicated by the downward pointing arrow beneath feature map 319, a 2×2 max pooling operation is performed on feature map 319 to produce feature map 320, wherein feature map 320 is of half the spatial resolution of feature map 319. Additionally, feature map 319 is copied, cropped, and concatenated with output from feature map 336 to produce feature map 338, as indicated by the dash-tailed rightward pointing arrow immediately to the right of feature map 319.

As indicated by the solid black rightward pointing arrow immediately to the right of feature map 320, a 3×3 convolution with stride 1 is performed on feature map 320 to produce feature map 322.

As indicated by the solid black rightward pointing arrow immediately to the right of feature map 322, a 3×3 convolution with stride 1 is performed on feature map 322 to produce feature map 324.

As indicated by the downward pointing arrow beneath feature map 324, a 2×2 max pooling operation is performed on feature map 324 to produce feature map 326, wherein feature map 326 is of one fourth the spatial resolution of feature map 324. Additionally, feature map 324 is copied, cropped, and concatenated with output from feature map 330 to produce feature map 332, as indicated by the dash-tailed rightward pointing arrow immediately to the right of feature map 324.

As indicated by the solid black rightward pointing arrow immediately to the right of feature map 326, a 3×3 convolution is performed on feature map 326 to produce feature map 328.

As indicated by the solid black rightward pointing arrow immediately to the right of feature map 328, a 3×3 convolution with stride 1 is performed on feature map 328 to produce feature map 330.

As indicated by the upward pointing arrow immediately above feature map 330, a 2×2 up-convolution is performed on feature map 330 to produce a first half of feature map 332, while copied and cropped features from feature map 324 are used to produce a second half of feature map 332. Briefly, a 2×2 up-convolution (herein also referred to as a deconvolution, or up-sampling) with stride of 2, includes mapping a single feature in a single feature channel of an immediately preceding feature map to four features distributed amongst four feature channels in a current feature map (that is, output from a single feature channel is taken as input by four feature channels). Up-convolution/deconvolution/up-sampling comprises projecting a feature value, from a single feature channel, through a deconvolution filter (also herein referred to as a deconvolution kernel) to produce a plurality of outputs.

As indicated by the solid black rightward pointing arrow immediately to the right of feature map 332, a 3×3 convolution is performed on feature map 332 to produce feature map 334.

As indicated by the solid black rightward pointing arrow immediately to the right of feature map 334, a 3×3 convolution is performed on feature map 334 to produce feature map 336.

As indicated by the upward pointing arrow immediately above feature map 336, a 2×2 up convolution is performed on feature map 336 to produce half of feature map 338, while copied and cropped features from feature map 318 produce the second half of feature map 338.

As indicated by the solid black rightward pointing arrow immediately to the right of feature map 338, a 3×3 convolution is performed on feature map 338 to produce feature map 340.

As indicated by the solid black rightward pointing arrow immediately to the right of feature map 340, a 3×3 convolution is performed on feature map 340 to produce feature map 342.

As indicated by the upward pointing arrow immediately above feature map 342, a 2×2 up convolution is performed on feature map 342 to produce a first half of feature map 344, while copied and cropped features from feature map 312 are used to produce the second half of feature map 344.

As indicated by the solid black rightward pointing arrow immediately to the right of feature map 344, a 3×3 convolution is performed on feature map 344 to produce feature map 346.

As indicated by the solid black rightward pointing arrow immediately to the right of feature map 346, a 3×3 convolution is performed on feature map 346 to produce feature map 348.

As indicated by the upward pointing arrow immediately above feature map 348, a 2×2 up convolution is performed on feature map 348 to produce a first half of feature map 350, while copied and cropped features from feature map 306 are used to produce the second half of feature map 350.

As indicated by the solid black rightward pointing arrow immediately to the right of feature map 350, a 3×3 convolution is performed on feature map 350 to produce feature map 352.

As indicated by the solid black rightward pointing arrow immediately to the right of feature map 352, a 3×3 convolution is performed on feature map 352 to produce feature map 354.

As indicated by the hollow headed rightward pointing arrow immediately to the right of feature map 354, a 1×1 convolution is performed on feature map 354 to produce output layer 356a. Briefly, a 1×1 convolution includes a 1-to-1 mapping of feature channels in a first feature space to feature channels in a second feature space, wherein no reduction in spatial resolution occurs.

The one or more features per channel in output layer 356a may correspond to a predicted ultrasound image. Output layer 356a may comprise an output layer of neurons, wherein each neuron may correspond to a pixel of a predicted ultrasound image.

In this way, CNN architecture 300 may enable mapping of an ultrasound image to an output. CNN architecture 300 illustrates the feature map transformations which occur as an input image tile is propagated through the neuron layers of the convolutional neural network, to produce predicted output.

The weights (and biases) of the convolutional layers in the neural network 300 are learned during training, as will be discussed in more detail with reference to FIG. 6 below. Briefly, a loss function is defined to reflect the difference between the predicted output and the ground truth output. The difference/loss may be back projected to the neural network to update the weights (and biases) of the convolutional layers. A plurality of training data pairs, comprising ultrasound images and corresponding ground truth outputs, may be used to train CNN 300.

It will be appreciated that the current disclosure encompasses neural network architectures comprising one or more regularization layers, including batch normalization layers, dropout layers, Gaussian noise layers, and other regularization layers known in the art of machine learning which may be used during training to mitigate overfitting and increase training efficiency while reducing training duration. Regularization layers are used during CNN training and deactivated or removed during post training implementation of the CNN. These layers may be interspersed between the layers/feature maps shown in FIG. 3, or may replace one or more of the shown layers/feature maps.

It should be understood that the architecture and configuration of CNN 300 shown in FIG. 3 is for illustration, not for limitation. Any appropriate neural network can be used, such as ResNet, recurrent neural networks, General Regression Neural Network (GRNN), etc. One or more specific embodiments of the present disclosure are described above in order to provide a thorough understanding. These described embodiments are only examples of machine learning models which may benefit from training on more varied training data, and a larger volume of training data, as may be achieved by modifying existing ultrasound training data using the methods disclosed herein. The skilled artisan will understand that specific details described in the embodiments can be modified when being placed into practice without deviating the spirit of the present disclosure.

Referring to FIG. 4, a flow chart of a method 400 for generating augmented ultrasound training data is shown. Method 400 may be implemented by one or more of the above disclosed systems, such as image processing system 202. Method 400 may be implemented as part of a machine learning model training routine to increase a number of training data pairs on which the machine learning model trains, by introducing/simulating one or more modifications. In one example, augmented training images may be generated by method 400 on demand, that is, method 400 may produce new augmented ultrasound images for machine learning model training on an as-needed basis. Method 400 may enable a machine learning model to become less sensitive to minor changes in noise, contrast, etc., thereby enabling training of a more robust and generalizable model.

Method 400 begins at operation 402, where the image processing system selects an ultrasound training data pair comprising an ultrasound image and a ground truth output. As discussed previously, ground truth output comprises an expected, ideal, or "correct" result from a machine learning model based on input of the ultrasound image. In one example, in a machine learning model trained to segment an ultrasound image into background and foreground, a ground truth output corresponding to a specific ultrasound image may comprise an expert curated segmentation map of the ultrasound image. In other examples, the ground truth output may comprise expert generated classification data. In another example, the ground truth output may be produced by an analytical method/algorithm.

At 404, the image processing system determines one or more modifications to apply to the selected ultrasound image of the selected training data pair. The process of selecting modifications to apply to the ultrasound image is discussed in more detail in reference to FIG. 5. Briefly, in one embodiment, determining a modification to apply to an ultrasound image may comprise generating a random number, constraining the random number to be within a pre-determined heuristic range, wherein in one example a heuristic range is determined by an expert and stored within non-transitory memory, therefore constraining the modifications to more closely reflect deviations/variations likely to occur in real ultrasound images. In one example, the random number may be used to determine a type of modification, or a plurality of types of modifications to apply to the ultrasound image.

In one example, modifications may comprise simulating a field of view change of the ultrasound image, such as by widening an ultrasound image and padding the blank margins of the ultrasound image with ultrasound data taken from another ultrasound image and/or synthesized via a generative network/model. In another example, the modification may comprise simulating a narrower scan region by cropping the ultrasound image, and randomly determining an extent of cropping, wherein the extent of cropping is constrained to a pre-determined range. In another example, a modification may comprise blurring/distorting an ultrasound image, such as by inclusion of rib shadows, speckle noise, or reverberations from strong reflectors. In another example, both a field of view modification and an artifact modification may be added to the ultrasound image. In another example, following addition of the modification the image processing system may determine if the produced augmented ultrasound image has been used previously to train a same machine learning network, and upon a determination that the augmented ultrasound image has been previously used, the image processing system may add one or more additional modifications to the ultrasound image, to differentiate it from the previously used ultrasound image. In one example, a plurality of modifications is randomly selected, wherein each of the modifications simulates a likely deviation in an ultrasound image, thereby reducing a probability that a same modification will be applied to a same ultrasound image. In other words, by randomly selecting a plurality of modifications and parameters of the plurality of modifications, a probability that a machine learning model will be trained using a same ultrasound image twice is substantially reduced.

At 406, the image processing system applies the one or more determined modifications to the ultrasound image to produce an augmented ultrasound image. FIGS. 7 and 8 show two specific examples of augmented ultrasound images produced by applying modifications to un-augmented ultrasound images.

At 408, the image processing system modifies the ground truth output based on the modifications applied to the ultrasound image, to produce an augmented ground truth output. In one embodiment, spatially distorting an ultrasound image may correspondingly alter an expected output of a machine learning model, and therefore applying the same spatial distortion to the ground truth output may maintain the relationship between the ultrasound image and the ground truth output. In other words, the augmented ground truth output comprises an expected output of a machine learning model based on input of the augmented ultrasound image. In one example, a machine learning model is trained to locate anatomical keypoints on an Ultrasound image of the heart based on input images, therefore, modifications made to the input image pixel values, such as adding noise, adding Ultrasound noise and shadows, making the image brighter or darker, making the contract lower or saturated etc. may have no effect on the output coordinates of the anatomical keypoints to be located. On the other hand, geometric transformations such as translation, rotation, zoom or even non-rigid transformations may need to be applied to the ground truth coordinates in the same way they are applied to the image in order to maintain validity of the ground truth coordinates.

Figure 6:
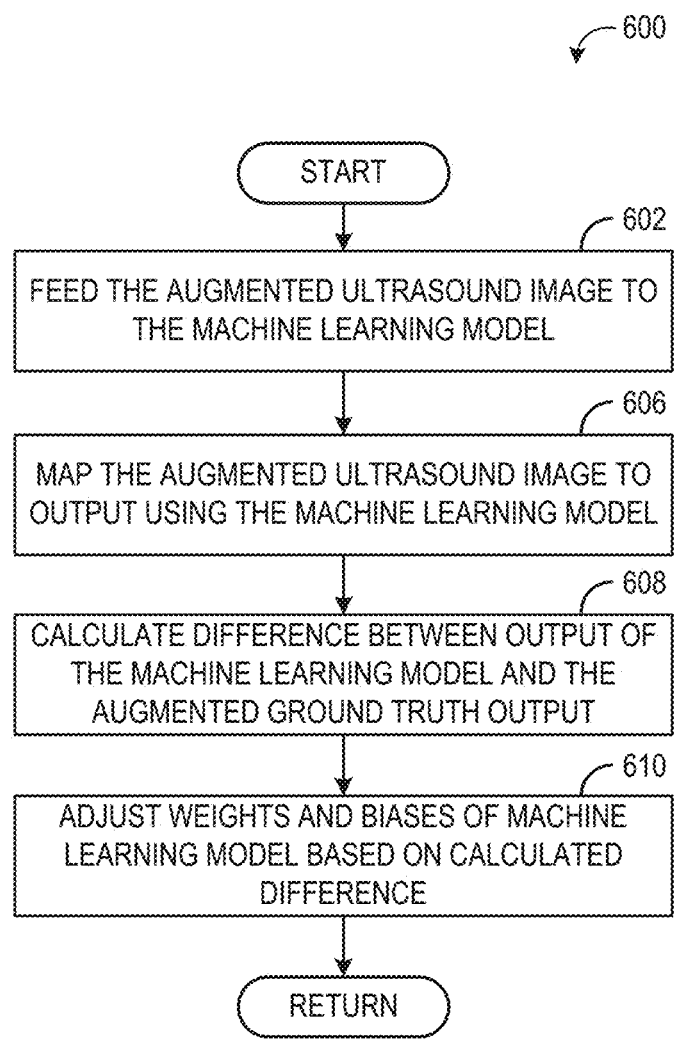
FIG. 6 is a flow chart illustrating a method for training a deep learning network using augmented ultrasound images, according to an exemplary embodiment.

At 410, method 400 includes training the machine learning model, as discussed in more detail in reference to FIG. 6. Briefly, the augmented training data pair comprising the augmented ultrasound image and the augmented ground truth output may be fed to a machine learning model, wherein the machine learning model may have not encountered the augmented ultrasound image in previous training iterations, as the randomly applied modifications may significantly reduce a probability of a same augmented ultrasound image being used to train a same machine learning model twice.

At 412, the image processing system evaluates if the machine learning model training is complete. In one example, training may terminate upon a rate of parameter change decreasing to below a threshold. In another example, a training process may end upon greater than a threshold degree of accuracy being achieved by the model on a training data set. In one embodiment, a threshold degree of prediction accuracy may be set, and upon the machine learning model producing output which deviates from the ground truth output by less than the threshold, a training process of the machine learning model may be ended and the model stored, as at 414.

However, if at 412 it is determined that the machine learning model is not trained, method 400 may return to select another ultrasound image and another corresponding ground truth output, as at 402. Method 400 may then proceed through steps 404-412 repeatedly until the image processing system determines that that machine learning model training is complete.

In this way, method 400 enables a machine learning model to be trained on a finite pool of ultrasound image training data, while mimicking a substantially larger training data set by applying random or pseudo-random ultrasound specific modifications to the ultrasound images of the training data set. In other words, by applying random degrees of modifications, a machine learning model may perform with higher fidelity on real world data, which may comprise various deviations from the base ultrasound image training data set.

Figure 5:
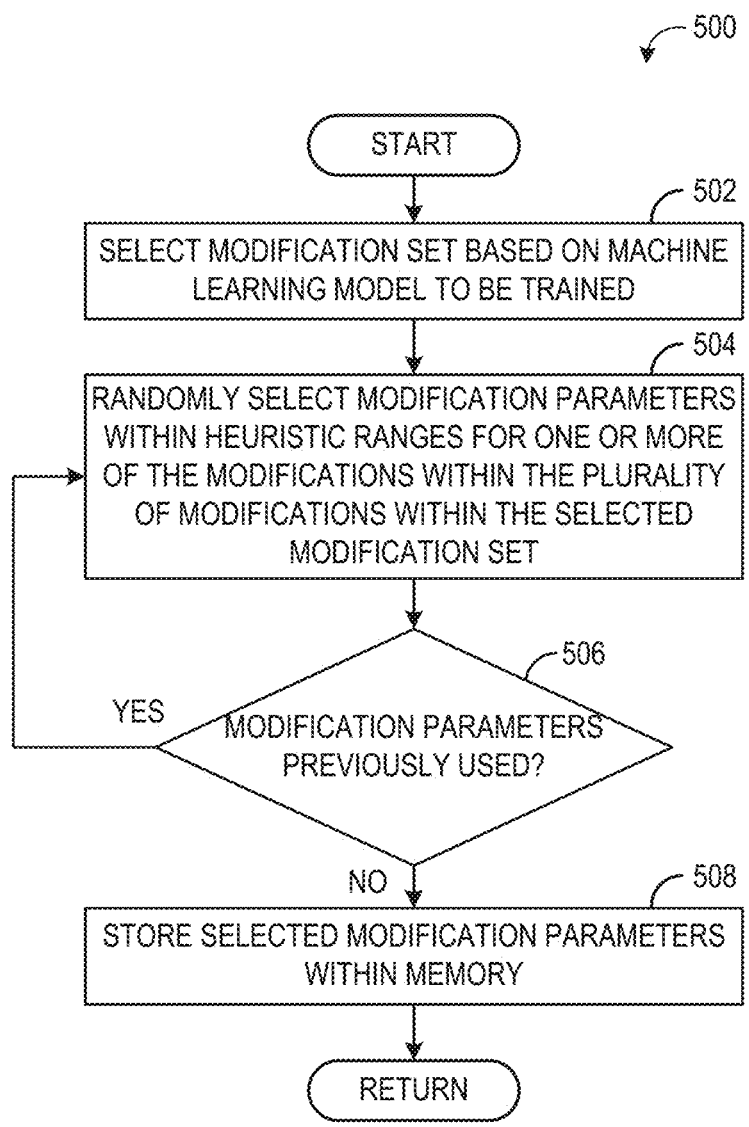
FIG. 5 is a flow chart illustrating a method for determining modifications to apply to an ultrasound image to produce an augmented ultrasound image, according to an exemplary embodiment.

Turning to FIG. 5, an example method 500 for determining modifications to apply to an ultrasound image is shown. Method 500 may be executed by an image processing system based on instructions stored in non-transitory memory. In one example, method 500 may be executed as part of method 400.

Method 500 begins at 502, where the image processing system selects a set of modifications based on the machine learning model to be trained. In one embodiment, the image processing system may comprise a plurality of different types of modifications, and based on a type of ultrasound image being processed by a machine learning model, or further based upon the processing being performed by the machine learning model, a distinct subset of the plurality of types of modifications may be selected. In one example, a machine learning model to be trained comprises a convolutional neural network to be trained to detect a pathology in an imaged anatomical region, and based on this a subset of modifications may be selected.

At 504, the image processing system randomly selects modification parameters within heuristic ranges for each parameter of each modification to be applied to the ultrasound image. In one example, 504 may include generating random numbers using a random number generator, and constraining the random numbers generated to be within pre-determined ranges for each of the types of modifications using a remainder operator. In a specific example, a field of view modification may be randomly selected by generating a first random number corresponding to the type of field of view change (a change in depth, a change in azimuthal angle, etc.) and a second random number may be generated to determine an extent of the field of view change (how much depth change simulation, how much is the azimuthal angle to change. etc.). In another example, a type, size, and placement within an ultrasound image of an ultrasound image artifact may be randomly selected by generating a first, second, and third random number, and selecting the type, size, and placement based on the first, second, and third random numbers respectively. In one embodiment, a modification comprises an ultrasound image artifact, wherein the ultrasound image artifact comprises one or more of rib shadows, clutter noise, reverberations from strong reflectors, and speckle noise, and wherein the random number is used to determine a position within the ultrasound image of the ultrasound image artifact.

At 506, the image processing system may evaluate if the randomly selected modifications have been previously applied to the current ultrasound image. If the randomly selected modifications have been previously applied to the current ultrasound image, method 500 returns to 504, where new modification parameters are selected. However, if at 506 it is determined that the randomly selected modifications have not been previously applied to the current ultrasound image, method 500 may proceed to store the selected modification parameters within memory, as at 508. By storing the selected modification parameters within memory, the image processing system may determine during future iterations of method 500 if a same set of modification parameters has been previously used with a same ultrasound image. In this way, a probability that a machine learning model will be trained using duplicates of the same ultrasound image, with the same modifications, is reduced substantially.

In this way, method 500 enables an image processing system to generate a substantially endless series of novel training for use in training one or more machine learning models, thereby reducing a probability that the machine learning models will over fit a finite pool of training data, which may increase the robustness and generalizability of the model. Further, by selecting set of modifications to apply to ultrasound images based on the types of machine learning models being trained and the use case, machine learning models more specifically tailored for particular real world applications use may be trained.

Referring to FIG. 6, a flow chart of a method 600 for training a deep neural network (such as CNN 300 shown in FIG. 3) is shown, according to an exemplary embodiment. Method 600 may be implemented by any of the above disclosed systems, such as image processing system 202 or ultrasound imaging system 100. In some embodiments, method 600 may be implemented as executable instructions in an imaging device, an edge device connected to the imaging device, a cloud in communication with the imaging device, or any appropriate combination thereof.

Method 600 begins at operation 602, where an augmented ultrasound image is fed to the machine learning model. In some embodiments, the augmented ultrasound image may be stored in the image processing system, such as in ultrasound image data 212 of image processing system 202. In other embodiments, the augmented ultrasound image may be acquired via communicative coupling between the image processing system and an external storage device, such as via Internet connection to a remote server.

At operation 604, the machine learning model maps the input augmented ultrasound image to output. In one example, the machine learning model maps the input augmented ultrasound image to output by propagating a plurality of pixel intensity values input at an input layer through a plurality of layers, as described in more detail with reference to FIG. 3 and CNN architecture 300.

At operation 608 the output is compared to an augmented ground truth output corresponding to the augmented ultrasound image. In one embodiment, step 608 includes calculating a difference between the output of the machine learning model and the augmented ground truth output, wherein the difference may be used to calculate a loss function for use in a gradient descent algorithm to adjust one or more parameter weights of the machine learning model.

At operation 610, the weights and biases of the machine learning network are adjusted based on the difference between the output and the augmented ground truth output calculated in operation 608. The difference (or loss), as determined by the loss function, may be back propagated through the neural learning network to update the weights (and biases) of the machine learning model. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the deep neural network is then updated by adding the negative of the product of the gradient determined (or approximated) for the weight (or bias) with a predetermined step size. Method 500 may then end. It will be noted that method 600 may be repeated until the weights and biases of the deep neural network converge, or the rate of change of the weights and/or biases of the deep neural network for each iteration of method 600 are under a threshold.

Turning to FIG. 7, an example of an ultrasound image 710, and a corresponding augmented ultrasound image 712 produced by applying one or more ultrasound specific modifications is shown. Ultrasound image 710 comprises an ultrasound image such as may be acquired by ultrasound imaging system 100, wherein ultrasound image 710 may be referred to herein as an un-augmented ultrasound image. Ultrasound image 710 may be used in conjunction with one or more methods disclosed herein, such as method 400, to produce augmented ultrasound image 712. Augmented ultrasound image 712 includes one or more modifications selected and applied by an image processing system, thereby creating a new ultrasound image, distinct from the un-augmented ultrasound image 710. Specifically, augmented ultrasound image 712 includes the following applied modifications: a deeper scan depth was simulated by adding noise to create additional depth; a wider scan region was simulated, adding noise to the edges of the un-augmented image to simulate a wider field of view; an ultrasound shadow artifact was added by introducing a streak of noise through the un-augmented image 710; all pixel intensities had a constant value added and were then multiplied by a constant close to 1; and low intensity Gaussian noise was added to all pixels.

Turning to FIG. 8, another example of an un-augmented ultrasound image 810 and a corresponding augmented ultrasound image 812 is shown. Ultrasound image 810 comprises an ultrasound image such as may be acquired by ultrasound imaging system 100, wherein ultrasound image 810 may be referred to herein as an un-augmented ultrasound image. Ultrasound image 810 may be used in conjunction with one or more methods disclosed herein, such as method 400, to produce augmented ultrasound image 812. Augmented ultrasound image 812 includes one or more modifications selected and applied by an image processing system, thereby creating a new ultrasound image, distinct from the un-augmented ultrasound image 810. Specifically, augmented ultrasound image 812 includes the following modifications: a wider scan region was simulated by adding noise to the edges of the un-augmented image 810 to simulate a wider field of view; an ultrasound shadow artifact was added by introducing a streak of noise through the un-augmented image 810; all pixel intensities had a constant value added and were then multiplied by a constant close to 1; and low intensity Gaussian noise was added to all pixels.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method comprising:
 selecting an ultrasound image and a ground truth output corresponding to the ultrasound image;

determining a first modification to apply to the ultrasound image;

applying the first modification to the ultrasound image to produce an augmented ultrasound image;

modifying the ground truth output based on the first modification to produce an augmented ground truth output corresponding to the augmented ultrasound image; and training a machine learning model to predict a segmentation map or reduce blurring using the augmented ultrasound image and the augmented ground truth output.

2. The method of claim 1, wherein determining the first modification comprises generating a random number and determining the first modification based on the random number.

3. The method of claim 2, wherein the modification comprises simulating a narrower scan region by cropping the ultrasound image, and wherein the random number is used to determine an extent of cropping.

4. The method of claim 2, wherein the modification comprises simulating a wider scan region by increasing a width of the ultrasound image, wherein the random number is used to determine an amount of increase of the width.

5. The method of claim 4, wherein simulating the wider scan region further comprises filling a blank margin of the wider scan region with ultrasound data.

6. The method of claim 5, wherein the ultrasound image is a first ultrasound image, and wherein the ultrasound data is obtained from a second ultrasound image.

7. The method of claim 5, wherein the machine learning model is a first machine learning model, and wherein the ultrasound data is produced by a second machine learning model trained to simulate ultrasound data.

8. The method of claim 2, wherein the first modification comprises an ultrasound image artifact, wherein the ultrasound image artifact comprises one or more of rib shadows, clutter noise, reverberations from strong reflectors, and speckle noise, and wherein the random number is used to determine a position within the ultrasound image of the ultrasound image artifact.

9. The method of claim 1, wherein the augmented ultrasound image is a first augmented ultrasound image and the augmented ground truth output is a first augmented ground truth output, the method further comprising:

determining a second modification to apply to the first augmented ultrasound image, wherein the second modification is different than the first modification;

applying the second modification to the first augmented ultrasound image to produce a second augmented ultrasound image;

modifying the first ground truth output based on the second modification to produce a second augmented ground truth output corresponding to the second augmented ultrasound image; and training the machine learning model using the second augmented ultrasound image and the second augmented ground truth output.

10. A method for augmenting ultrasound training data, the method comprising:

selecting an ultrasound training data pair from a plurality of ultrasound training data pairs, wherein the ultrasound training data pair comprises an ultrasound image and a ground truth output corresponding to the ultrasound image;

determining a plurality of modifications;

applying the plurality of modifications to the ultrasound image to produce an augmented ultrasound image;

modifying the ground truth output based on the plurality of modifications to produce an augmented ground truth output, wherein the augmented ground truth output corresponds to the augmented ultrasound image; and training a deep neural network to predict a segmentation map or reduce blurring using the augmented ultrasound image and the augmented ground truth output.

11. The method of claim 10, wherein determining the plurality of modifications comprises randomly or pseudo-randomly selecting a plurality of parameter values, wherein the plurality of modifications are determined based on the plurality of parameter values.

12. The method of claim 11, wherein randomly or pseudo-randomly selecting the plurality of parameter values further comprises constraining the parameter values to be within a pre-determined heuristic range.

13. The method of claim 10, wherein the plurality of parameter values is used to determine a size, a position within the ultrasound image, and a type of ultrasound image artifact, and wherein applying the plurality of modifications to the ultrasound image to produce the augmented ultrasound image comprises adding an ultrasound image artifact of the size and the type determined by the plurality of parameter values to the position within the ultrasound image determined by the plurality of parameter values.

14. The method of claim 10, wherein the plurality of modifications is a first plurality of modifications, the augmented ultrasound image is a first augmented ultrasound image, and the augmented ground truth output is a first augmented ground truth output, the method further comprising:

re-selecting the ultrasound training data pair from the plurality of ultrasound training data pairs, wherein the ultrasound training data pair comprises the ultrasound image and the ground truth output corresponding to the ultrasound image;

determining a second plurality of modifications, wherein the second plurality of modifications is not equivalent to the first plurality of modifications;

applying the second plurality of modifications to the ultrasound image to produce a second augmented ultrasound image;

modifying the ground truth output based on the second plurality of modifications to produce a second augmented ground truth output, wherein the second augmented ground truth output corresponds to the second augmented ultrasound image; and training the deep neural network using the second augmented ultrasound image and the second augmented ground truth output.

15. The method of claim 10, wherein training the deep neural network using the augmented ultrasound image and the augmented ground truth output comprises:

feeding the augmented ultrasound image to the deep neural network;

predicting an output from the deep neural network based on the augmented ultrasound image;

determining a difference between the output and the augmented ground truth output; and adjusting one or more parameters of the deep neural network based on the difference between the output and the augmented ground truth output.

16. An image processing system comprising:

a memory storing a plurality of training data pairs and instructions; and a processor communicably coupled to the memory and when executing the instructions, configured to:
  select an ultrasound image and a ground truth output corresponding to the ultrasound image;
  determine a first modification to apply to the ultrasound image;
  apply the first modification to the ultrasound image to produce an augmented ultrasound image;
  modify the ground truth output based on the first modification to produce an augmented ground truth output corresponding to the augmented ultrasound image; and
  train a machine learning model to predict a segmentation map or reduce blurring using the augmented ultrasound image and the augmented ground truth output.

17. The image processing system of claim 16, wherein the first modification comprises simulating a scan depth change by altering a size of one or more anatomical features imaged by the ultrasound image, wherein an extent of altering of the size of the one or more anatomical features is selected from a pre-determined range of sizes.

18. The image processing system of claim 16, wherein the augmented ultrasound image is a first augmented ultrasound image and the augmented ground truth output is a first augmented ground truth output, and wherein upon executing the instructions the processor is further configured to:
  re-select the ultrasound image and the ground truth output corresponding to the ultrasound image;
  determine a second modification to apply to the ultrasound image, wherein the second modification is not equivalent to the first modification;
  apply the second modification to the ultrasound image to produce a second augmented ultrasound image;
  modify the ground truth output based on the second modification to produce a second augmented ground truth output corresponding to the second augmented ultrasound image; and
  train the machine learning model using the second augmented ultrasound image and the second augmented ground truth output.

19. The image processing system of claim 18, wherein the first modification comprises a simulating a scan depth change and wherein the second modification comprises simulating an ultrasound image artifact.

20. The image processing system of claim 16, wherein the processor is configured to:
  store the augmented ultrasound image and the augmented ground truth output as an augmented training data pair within the memory;
  input the augmented ultrasound image to the machine learning model to obtain an output; and
  train the machine learning model according to a difference between the output and the augmented ground truth output.

* * * * *